(12) United States Patent
Collins et al.

(10) Patent No.: US 9,567,562 B1
(45) Date of Patent: Feb. 14, 2017

(54) ALGAE DRYER AND HARVESTING APPARATUS

(71) Applicants: Ronny Collins, Durant, OK (US); Phillip Gene Shaffer, Denison, TX (US)

(72) Inventors: Ronny Collins, Durant, OK (US); Phillip Gene Shaffer, Denison, TX (US)

( * ) Notice: Subject to any disclaimer, the term of this patent is extended or adjusted under 35 U.S.C. 154(b) by 430 days.

(21) Appl. No.: 13/999,911

(22) Filed: Apr. 2, 2014

Related U.S. Application Data

(63) Continuation-in-part of application No. 13/999,154, filed on Jan. 17, 2014, now Pat. No. 9,206,388.

(51) Int. Cl.
*F26B 3/32* (2006.01)
*F26B 3/08* (2006.01)
*C12N 1/12* (2006.01)

(52) U.S. Cl.
CPC ..................................... *C12N 1/12* (2013.01)

(58) Field of Classification Search
CPC ............. C12N 1/12; F26B 25/04; B01D 29/64
USPC ......... 34/95.2, 95, 95.1, 519, 520, 372–374; 239/264, 689; 410/408, 409, 415
See application file for complete search history.

(56) References Cited

U.S. PATENT DOCUMENTS

| | | |
|---|---|---|
| 3,951,805 A | 4/1976 | Dodd |
| 4,137,159 A | 1/1979 | Sawyer |
| 4,255,261 A | 3/1981 | Dodd |
| 4,268,385 A | 5/1981 | Yoshikawa |
| 4,450,080 A | 5/1984 | Dodd |
| 4,465,600 A | 8/1984 | Dodd |
| 8,563,759 B2 | 10/2013 | Hutton et al. |
| 2012/0226061 A1 | 9/2012 | Shepherd |

*Primary Examiner* — Kenneth Rinehart
*Assistant Examiner* — John McCormack
(74) *Attorney, Agent, or Firm* — Randal D. Homburg

(57) ABSTRACT

An algae dryer defines an insulated and heated stationary drum within which is positioned a rotating arm extending an axial sprayer to spray a coat of algae on the inside of the drum with a second integrated opposing arm axially extending an offset scraper which engages the inner perimeter of the drum surface and removes the algae from the interior of the drum, depositing the dry algae scrapings into the bottom of the drum through a slot, further directing the harvested algae through an auger to a packaging or processing location.

8 Claims, 5 Drawing Sheets

ALGAE DRYER AND HARVESTING APPARATUS

This is a continuation-in-part of application Ser. No. 13/999,154, filed on Jan. 17, 2014 by the same inventor. See Application Data Sheet filed with this application.

I. BACKGROUND OF THE INVENTION

1. Field of Invention

An algae dryer defines an insulated and heated stationary drum within which is positioned a rotating arm extending an axial sprayer to spray a coat of algae on the inside of the drum with a second integrated opposing arm axially extending an offset scraper which engages the inner perimeter of the drum surface and removes the algae from the interior of the drum, depositing the dry algae scrapings into the bottom of the drum through a slot, further directing the harvested algae through an auger to a packaging or processing location.

2. Description of Prior Art

A preliminary review of prior art patents was conducted by the applicant which reveal prior art patents in a similar field or having similar use. However, the prior art inventions do not disclose the same or similar elements as the present dryer and harvester apparatus, nor do they present the material components in a manner contemplated or anticipated in the prior art.

Most prior art patent involve a continuous belt that acts to deliver a skimmed algae from a pool, generally off the top layer of the pool. These type patent include several embodiments. The most recent published application in found in U.S. Patent App. No. 201226061 to Shepherd, and it involves a harvester including a main moving belt, a plurality of rollers and a motor for driving the belt in a continuous loop. There is a reactor tank and a vacuum extractor for applying a vacuum over a width of the belt to extract the biomass and to dry the main moving belt to an oil extraction device. Other belt driven skimmer harvesters are found in U.S. Pat. Nos. 4,465,600, 4,450,080, 4,255,261 and 3,951,805 to Dodd, U.S. Pat. No. 4,137,159 to Sawyer.

An algae filtration scrubber is disclosed in U.S. Pat. No. 6,837,991 to Norris. This algae scrubber system is used in a fish aquarium includes a partially submerged rotatable drum wrapped in plastic mesh as a anchor for algae growth, an effluent pipe shaped to match the perimeter of the rotating drum which withdraws water from a secondary tank and scrubs that water through the algae screen and returns the filtered water back to the secondary tank as refreshed. A centrifugal rotating disk assembly for waste water treatment, disclosed in U.S. Pat. No. 4,268,385 to Yoshikawa, includes a vertical disc made from a plurality of arcuate or radial impeller blades similar to a water wheel set over and partially within a trough filled with a waste water, the rotating disc exposing the water to air for the improved production of aerobic treatment by the greater surface of the exposed waste water to air.

II. SUMMARY OF THE INVENTION

Large scale algae production from a growth source for the conversion of the algae into a crude oil product for refinery into internal combustion fuels requires that the algae be harvested in some matter to evacuate the water content from the harvested algae into either a reduced water content slurry or preferably a dried product to reduce the transportation weight of the product and to make handling easier as a dry product than one that is liquid. This especially includes high output quantities of algae from high capacity algae growth means, including artificially grown algae from bioreactors and photobioreactors under optimal growth conditions. In prior patents filed by the same inventor, one dealing with a process for the accelerated growth of algae and the other for an improved photobioreactor, a single acre batter of photobioreactors has the capacity of producing enough algae to provide nearly 4500 barrels of crude oil algae product in a single day, with annual production from that acre providing algae growth converting to over 1.7 million barrels of crude oil per year. Thus, an improved dryer/harvester is necessary for the preparation and drying of this quantity of wet algae supply to either a wet slurry and in the case of the present harvester, a dry algae product which is delivered as a powder.

After draining a portion of the algae culture from the algae growth source or the photobioreactor, a wet algae product is produced. From a photobioreactor, a wet product is to be reduced from a water to algae content of approximately 93.4% water to algae to approximately 66% water to algae by means of a first stage drying, filtering or drainage apparatus prior to being transferred to the present harvester dryer. The water removed from the culture at this time is evacuated as captured water or vapor and removed to a recycled water storage tank or returned to the algae growth source for reuse. In some instances, this first stage product may be sent for refining as a liquid slurry whenever and if ever that technology becomes large scale.

The harvester dryer of the present invention is further provided to dry the liquid algae slurry and sprays it on a heated inner surface of a stationary cylinder, drying the algae spray nearly on contact in a flash drying manner, wherein a rotating blade traveling being a rotating spray bar scrapes the flash dried algae off the inner wall, causing the dry algae to fall to the bottom of the stationary cylinder through a linear lower channel into an auger basin, wherein the dried algae is moved by conveyor to a container for shipping to a refinery. Vapor from the second stage harvester apparatus is condensed back into a liquid state as it is returned to the recycled fresh water storage tank, or after cooling, to the algae growth source, providing a clean water source for reuse in the system or for other clean water purpose. It is a goal of the harvester dryer to present an environmentally friendly means to convert the algae product from a wet material to a dry material.

III. DESCRIPTION OF THE DRAWINGS

The following drawings are submitted with this utility patent application.

FIG. 6 is a diagram indicating the circulation of the steam from the steam generator to the algae drying and harvesting apparatus, and the recovery of the vapor and steam from the apparatus to the fresh water storage container for recycling to the steam generator for purpose of conservation of water.

IV. DESCRIPTION OF THE PREFERRED EMBODIMENT

Figure 1:
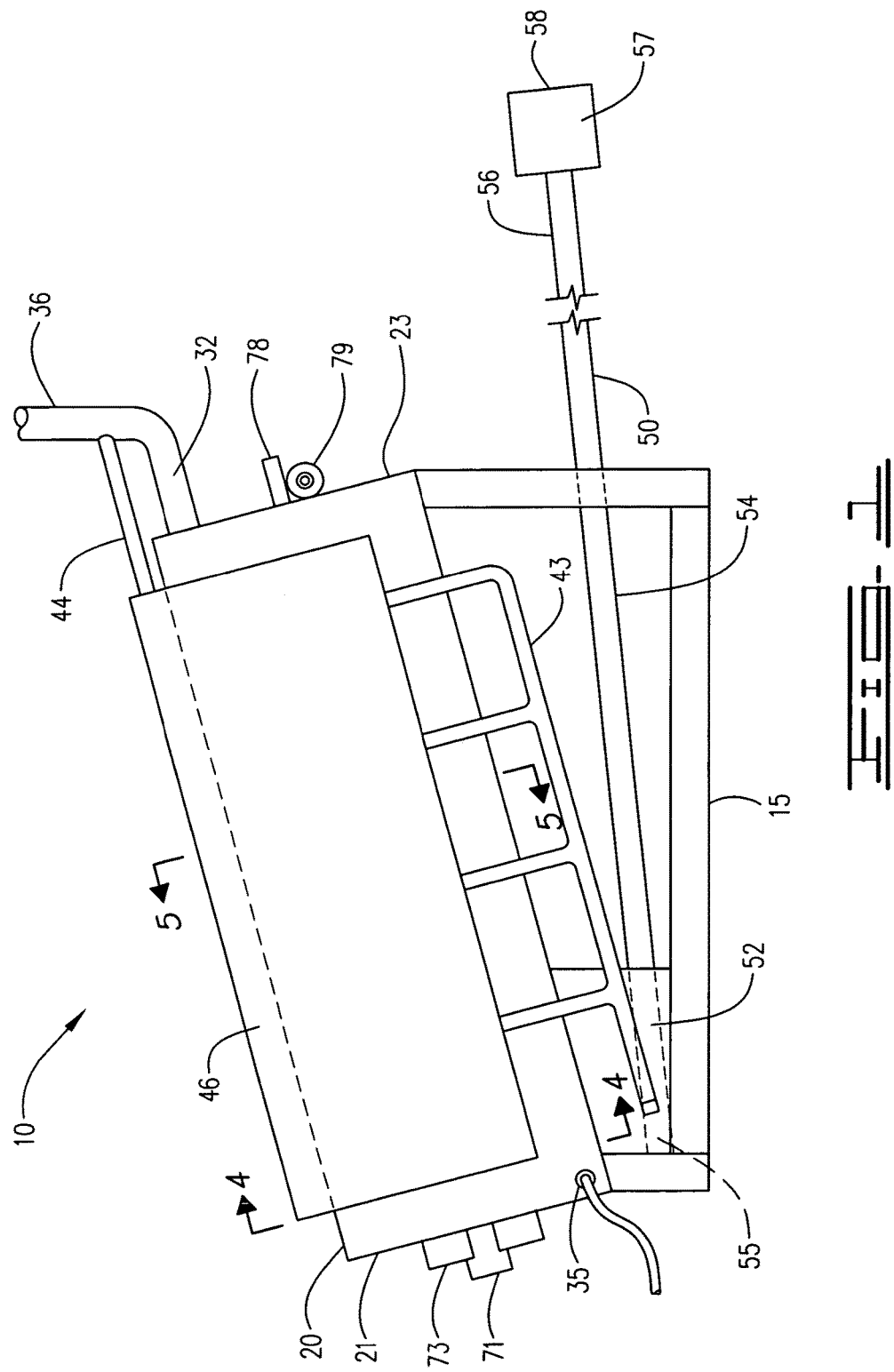
FIG. 1 is a side view of an algae drying and harvesting apparatus.
Figure 2:
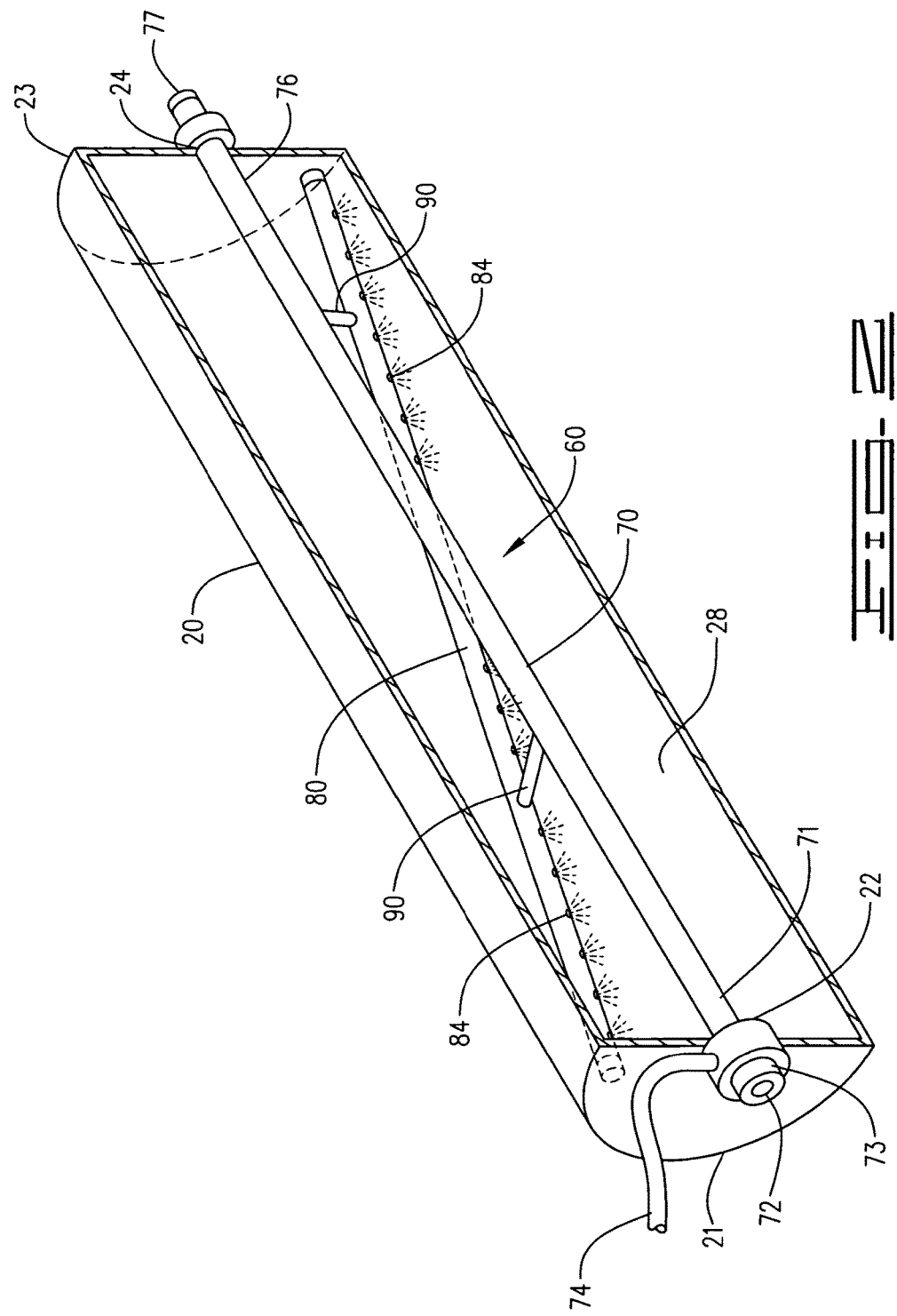
FIG. 2 is a perspective view of the interior of the drier vessel showing the rotating scraper and spray arm.
Figure 3:
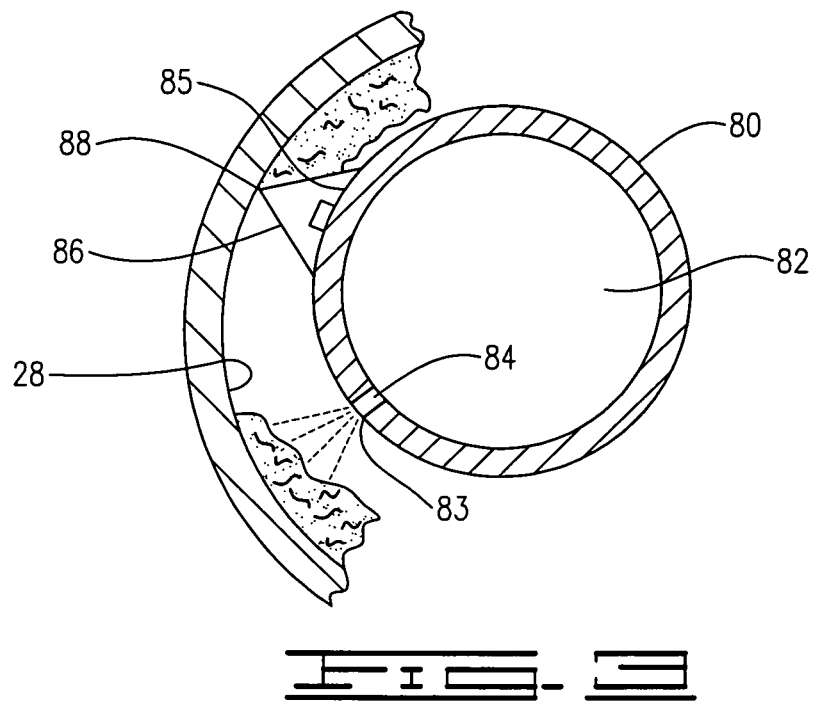
FIG. 3 is a side cross-sectional view of the scraper and spray arm scraping dried algae from the inner wall of the drier vessel while spraying the cleared drier wall with a fresh of wet algae slurry.
Figure 4:
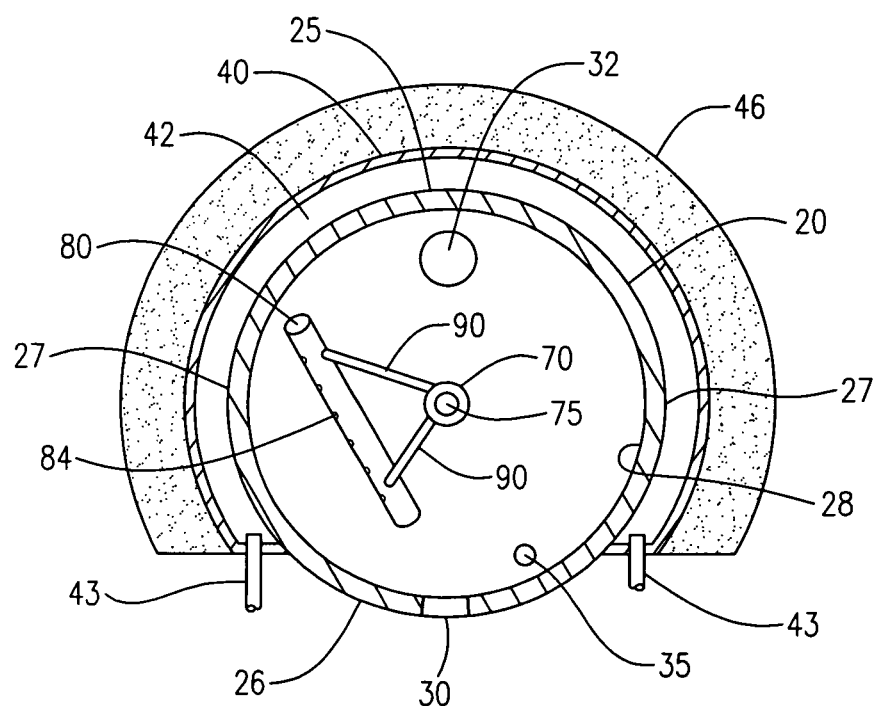
FIG. 4 is a cross-sectional view of the algae drying and harvesting apparatus indicating the drier vessel, the steam cavity and the insulating blanket layer with a position of the scraper and spray arm within the drier vessel.
Figure 5:
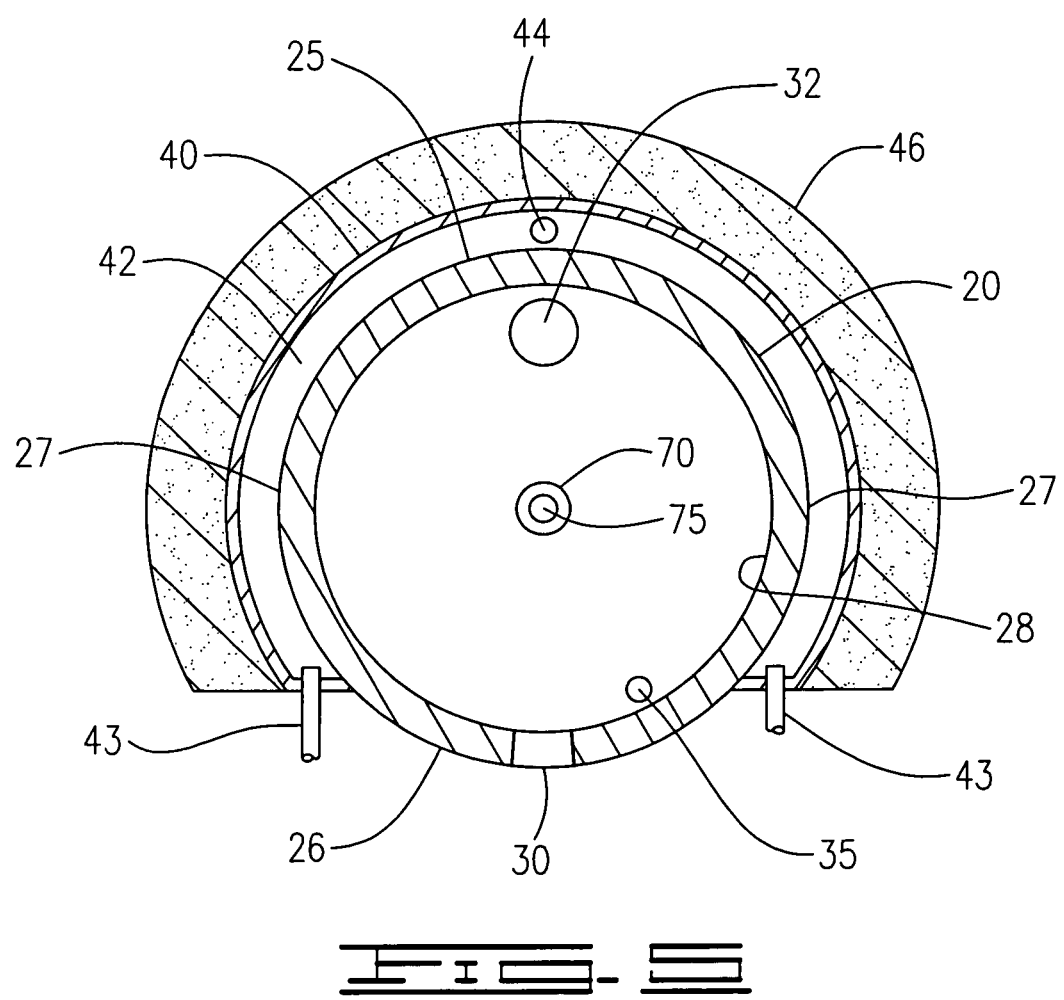
FIG. 5 is a cross sectional view of the algae drying and harvesting apparatus indicating the drier vessel, the steam cavity and the insulating blanket layer including the steam inlet tubes, the vapor outlet port and the steam outlet port.
Figure 5:
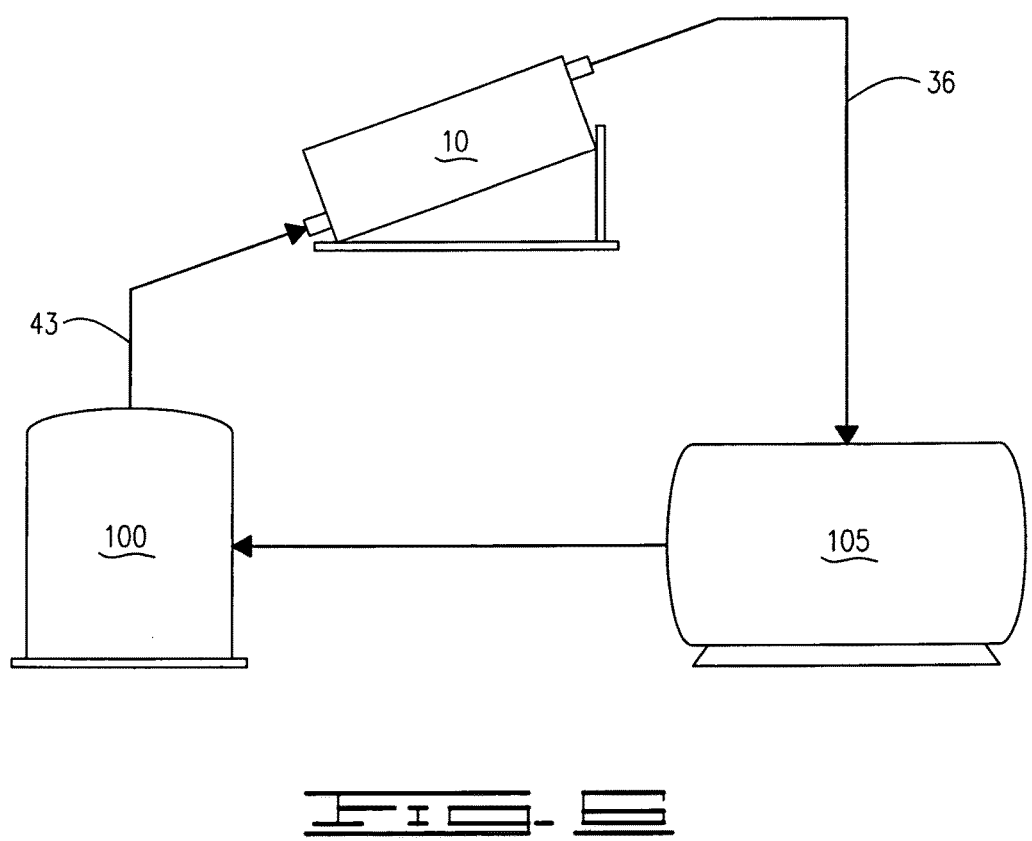

An algae drying and harvesting apparatus 10 for a large scale conversion of a liquid algae slurry into a dried algae composition, primarily for the purpose of providing the dried algae for transport and subsequent conversion to a crude oil product, the apparatus 10 comprising a ground support frame 15, FIG. 1, upon which a cylindrical drier vessel 20 is mounted, the ground support frame 15 placing the drier vessel 20 in an elevating diagonal position from a lower end 21 to an upper end 23, the lower end 21, FIG. 2, providing a lower central aperture 22 and the upper end 23 providing an upper central aperture 24, the drier vessel 20 further defining an upper outer surface 25, a lower outer surface 26 and two lateral outer surfaces 27, an upper steam chamber 40 attached to at least the upper outer surface 25 and two lateral outer surfaces 26, the upper steam chamber 40 defining a steam cavity 42 supplied by at least one steam manifold 43 providing steam from an outer steam generator 100, FIGS. 1 and 4-7, the steam cavity 42 in direct communication with the contact outer surfaces 25,26, of the drier vessel 20, conductively heating an inner wall 28 of the drier vessel 20 to a high temperature and a steam outlet port 44 through which exhaust steam may be diverted for recovery, recycling and reuse, an insulating blanket layer 46, FIGS. 1 and 4-5, over the upper steam chamber 40 to reduce heat loss to the upper steam chamber 40 regardless of the environment within which the apparatus 10 is located, a scraper and sprayer assembly 60, FIGS. 2-4, having a central rotating tube 70 extending through the lower central aperture 22 and the upper central aperture 24, the central rotating tube 70 defining a lower end 71 having an end cap 72 and attaching to a universal hose connection 73, FIG. 2, further attached to a hose 74 delivering the liquid algae slurry into an inner longitudinal bore 75 within the central rotating tube 70 and an upper end 76 having an end cap 77, with the upper end 76 of the central rotating tube 70 defining an outer drive portion 78 connected to a rotating drive motor 79, FIG. 1, to rotate the central rotating tube 70 within the drier vessel 20, the central rotating tube 70 further attaching a scraper and spray bar member 80, the scraper and spray bar member 80 defining an inner throat 82 from which a plurality of liquid spray ports 84 are defined along a lower margin 83 within and an angled scraper 86 defined on an outer margin 85 of the scraper and spray bar member 80, the scraper and spray bar member 80 attached to the central rotating tube 70 by at least two hollow transfer struts 90 providing a liquid communication between the inner longitudinal bore 75 of the central rotating tube 70 through the at least two hollow transfer struts 90 into the inner throat 82 and out the plurality of liquid spray ports 84, directing the liquid algae slurry onto the steam heated inner wall 28 of the drier vessel 20, FIG. 3, for flash drying of the algae slurry, after which the dried algae is removed by the scraper 86 on the scraper and spray bar member 80 at the next rotational pass into the lower end 21 of the drier vessel 20, and an auger assembly 50, FIG. 1, defining a lower dry algae bin 52 positioned below a drier vessel slot 30 in the lower outer surface 26 near the lower end 21 of the drier vessel 20, the auger assembly 50 further defining an auger 54 having a lower end 55 within the lower dry algae bin 52 and an upper end 56 having an auger drive motor 57 to direct the dry algae to a release outlet 58 for transfer to a directed location. The drier vessel 20 may also include a hydration monitoring means 35, FIGS. 1 and 4-5, within the lower end 21 to remotely monitor the moisture content of the dried algae within the drier vessel 20 and a vapor outlet port 32, FIGS. 1 and 4, to release the moisture and condensate from the drier vessel 20, the vapor outlet port 32 optionally connected to a vapor outlet tube 36 shared with the steam outlet port 44, FIG. 1, for diversion to an external fresh water storage container 105 for recover and recycling of clean water, FIG. 6.

It is preferred that the drier vessel 20 be a cylinder made from metal or other thermal conductive material with smooth inner walls 28 and that the upper steam chamber 40 be made from a material that can withstand containment of high heat steam under pressure without damage or deformity. As shown in FIGS. 4-5, it is preferred that the steam chamber 40 engage a majority of the drier vessel 20, especially those portions of the drier vessel 20 that would receive a constant coating of liquid algae slurry for drying and later scraping. As shown in FIG. 3, it is also shown that the scraper 86 is attached to the scraper and spray bar member 80 so that it could be replaced after wear to ensure perpetual contact with the inner walls 28 of the drier vessel 20 to avoid any potential accumulation of dried algae on the inner walls 28 of the drier vessel 20 and that the scraper 86 be optimally configured as shown with a scraper edge 88 being radially presented from scraper and spray bar member 80. The plurality of liquid spray ports 84 would be positioned behind the pathway of the scraper 86, shown in FIG. 3, with a spray angle from the scraper and spray bar member 80 as indicated in FIG. 3. It is also contemplated that the upper and lower central apertures 24, 22, be provided with a water sealed bearing, not shown, to allow the central rotating tube 70 of the sprayer and scraper assembly 60 to rotate with limited or nominal friction within the drier vessel 20 and to prevent any steam or water vapor to be released from the drier vessel 20 except through the vapor outlet port 32, further controlling the pressure and temperature within the drier vessel 20.

As indicated in FIGS. 1 and 4-5, the steam from the outer steam generator 100 would be preferably delivered to the steam cavity 42 by a manifold 43, which would more uniformly deliver to the steam cavity at more than one point and distribute the fresh hot steam under pressure to the upper steam chamber 40 for a more even distribution of heat to the contacting drier vessel 20. It is best that the algae within the drier vessel 20 be uniformly heated and dried so that the scraped dry algae product has been treated uniformly and produced a consistent dried algae product, as monitored by the hydration monitoring means 35 prior to removal from the drier vessel 20 into the dry algae bin 52 of the auger assembly 50 through the drier vessel slot 30.

The algae drying and harvesting apparatus 10 is primarily suited for the large scale of algae production for conversion into crude oil, where the algae product is to be delivered in a dried or dehydrated state for transport to a crude oil refinery. It is known in the art that certain algae is suitable for conversion to crude oil and eventually combustion fuels including diesel, gasoline and aviation fuel. In a large scale production, especially where the production of the algae is accomplished using a photobioreactor as disclosed in prior applications by the same inventor, large quantities of algae can be produced under controlled optimal conditions provided by these high production photobioreactors and, as mentioned in part under the prior patent application by the same inventor, wherein regulated temperature, lighting, pH and circulation conditions are supplied, the algae product is provided in a wet or liquid mixture. A first stage drying apparatus may be utilized to reduce the liquid to a higher algae to liquid water concentration. The present algae drying and harvesting apparatus takes that concentrated liquid algae and further dehydrates and flash dries the liquid algae slurry into a dry product which can be contained and transported as an unregulated and non-hazardous contained material not harmful to the environment for delivery to a refinery, rehydrated and then processed using known methods to extract the crude oil product which is further converted by known methods of refinement into the combustion fuels having the identical chemical properties as fuels derived from earth extracted petroleum crude oil.

Although being designed for the specific purpose indicated above, it should be realized that the apparatus 10 may be used for the drying of other products. Unique to this apparatus 10 is the drier vessel 20 remaining stationary during the drying process of the liquid materials, unlike the prior art patents that deal with a rotating drum or moving cylinder, similar to a cement mixer. The moving parts of the apparatus 10 are limited within the drier vessel 20 to the sprayer and scraper assembly 60, with the drive components of the sprayer and spray assembly 60 actually provided outside the drier vessel 20. This would significantly reduce the damage potential to the algae cells during the drying process supplied by the apparatus 10, delivering the algae is a healthier state and condition for further processing.

While the algae drying and harvesting apparatus 10 has been particularly shown and described with reference to a preferred embodiment thereof, it will be understood by those skilled in the art that changes in form and detail may be made therein without departing from the spirit and scope of the invention.

What is claimed is:

1. A drying and harvesting apparatus for a large scale conversion of a liquid slurry into a dried product, the apparatus comprising:
    a ground support frame;
    a cylindrical drier vessel mounted upon said ground support frame in an elevating diagonal position from a lower end to an upper end, said lower end defining a lower central aperture and said upper end defining an upper central aperture, said drier vessel further defining an upper outer surface, a lower outer surface, two lateral outer surfaces, an inner wall and a drier vessel slot in said lower outer surface at said lower end;
    an upper steam chamber attached to said upper outer surface and said two lateral outer surfaces, said upper steam chamber defining a steam cavity supplied by at least one steam manifold providing steam from an outer steam generator, said steam cavity in direct communication with said outer surfaces of said drier vessel conductively heating said inner wall of said drier vessel with a steam outlet port through which exhaust steam may be diverted for recovery, recycling and reuse;
    an insulating blanket layer over said upper steam chamber to eliminate heat loss to said upper steam chamber regardless of the environment within which said apparatus is located;
    a scraper and sprayer assembly defining having a central rotating tube extending through said lower central aperture and said upper central aperture, said central rotating tube providing a lower end having an end cap and attaching to a universal hose connection attached to a hose supplying said liquid slurry into an inner longitudinal bore within said central rotating tube and an upper end having an end cap, with said upper end of said central rotating tube defining an outer drive portion connected to a rotating drive motor rotating said central rotating tube within said drier vessel, said central rotating tube further attaching a scraper and spray bar member, said scraper and spray bar member defining an inner throat from which a plurality of liquid spray ports are defined along a lower margin within and an angular scraper defined on an outer margin of said scraper and spray bar member, said scraper and spray bar member attached to said central rotating tube by at least two hollow transfer struts providing a liquid communication between said inner longitudinal bore of said central rotating tube through said at least two hollow transfer struts into said inner throat and out said plurality of liquid spray ports, directing said liquid slurry onto said steam heated inner wall of said drier vessel for flash drying of said slurry, after which said dried product is removed by said scraper on said scraper and spray bar member at the next rotational pass into said lower end of said drier vessel; and
    an auger assembly defining a lower dry product bin positioned below said drier vessel slot, an auger having a lower end within said lower dry product bin and an upper end having an auger drive motor to direct said dried product to a release outlet for transfer to a directed location.

2. The drying and harvesting apparatus as disclosed in claim 1, wherein said liquid slurry contains quantities of algae and said dried product is dried algae which, subsequent to harvest, is converted into a crude oil product.

3. The drying and harvesting apparatus as disclosed in claim 1, said drier vessel including a hydration monitoring means within said lower end to remotely monitor moisture content of said dried algae within said drier vessel.

4. The drying and harvesting apparatus as disclosed in claim 1, said drier vessel including a vapor outlet port to release moisture and condensate from said drier vessel, said vapor outlet port connected to a vapor outlet tube shared with said steam outlet port for diversion of said outlet steam and vapor to an external fresh water storage container for recover and recycling of condensed clean water.

5. The drying and harvesting apparatus as disclosed in claim 1, wherein said manifold is configured to deliver said steam to said steam cavity at more than one point and distribute fresh hot steam under pressure to said upper steam chamber for a more uniform distribution of heat to said drier vessel wherein said dried product would be uniformly heated and dried so that said scraped dried product will be been treated uniformly and produced a consistent dried product, as monitored by a hydration monitoring means within said lower end prior to removal from said drier vessel into said dry product bin of said auger assembly through said drier vessel slot.

6. The drying and harvesting apparatus as disclosed in claim 1, wherein said liquid slurry contains quantities of algae and said dried product is dried algae which, subsequent to harvest, is converted into a crude oil product; and
    said drier vessel including a hydration monitoring means within said lower end to remotely monitor moisture content of said dried algae within said drier vessel.

7. The drying and harvesting apparatus as disclosed in claim 1, wherein said liquid slurry contains quantities of algae and said dried product is dried algae which, subsequent to harvest, is converted into a crude oil product; and said drier vessel including a vapor outlet port to release moisture and condensate from said drier vessel, said vapor outlet port connected to a vapor outlet tube shared with said steam outlet port for diversion of said outlet steam and vapor to an external fresh water storage container for recover and recycling of condensed clean water.

8. The drying and harvesting apparatus as disclosed in claim 1, wherein said liquid slurry contains quantities of algae and said dried product is dried algae which, subsequent to harvest, is converted into a crude oil product; and said manifold is configured to deliver said steam to said steam cavity at more than one point and distribute fresh hot steam under pressure to said upper steam chamber for a more uniform distribution of heat to said drier vessel wherein said dried product would be uniformly heated and dried so that said scraped dried product will be been treated uniformly and produced a consistent dried product, as monitored by a hydration monitoring means within said lower end prior to removal from said drier vessel into said dry product bin of said auger assembly through said drier vessel slot.

\* \* \* \* \*